US008551027B2

(12) United States Patent
Endo et al.

(10) Patent No.: US 8,551,027 B2
(45) Date of Patent: Oct. 8, 2013

(54) ASSIST DEVICE

(75) Inventors: Yosuke Endo, Wako (JP); Keishiro Kikuchi, Wako (JP); Ritsuo Hara, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 1150 days.

(21) Appl. No.: 12/484,523

(22) Filed: Jun. 15, 2009

(65) Prior Publication Data

US 2010/0049333 A1 Feb. 25, 2010

(30) Foreign Application Priority Data

Aug. 25, 2008 (JP) ................................ 2008-215456
Dec. 1, 2008 (JP) ................................ 2008-306349

(51) Int. Cl.

| | |
|---|---|
| ***A61F 5/37*** | (2006.01) |
| ***A61F 5/00*** | (2006.01) |
| ***A61B 19/00*** | (2006.01) |
| ***A63B 24/00*** | (2006.01) |
| ***A63B 21/005*** | (2006.01) |
| ***A61H 7/00*** | (2006.01) |
| ***A61H 1/02*** | (2006.01) |
| ***A61H 5/00*** | (2006.01) |

(52) U.S. Cl.
USPC ............... 601/5; 128/846; 128/869; 128/882; 482/4; 482/6; 482/7; 601/23; 601/33; 601/34; 601/35; 602/5; 602/16; 602/19; 602/23

(58) Field of Classification Search
USPC ............ 602/5, 16, 19, 23; 128/846, 869, 882; 482/4, 6, 7, 587; 601/5, 23, 33, 34, 35
See application file for complete search history.

(56) References Cited

U.S. PATENT DOCUMENTS

2003/0093021 A1* 5/2003 Goffer ............................ 602/23
2005/0251079 A1* 11/2005 Carvey et al. .................. 602/26
2010/0280629 A1* 11/2010 Jung et al. ....................... 623/53

FOREIGN PATENT DOCUMENTS

JP 10-304502 11/1998
JP 2005-271613 10/2005

* cited by examiner

*Primary Examiner* — Patricia Bianco
*Assistant Examiner* — Brandon L Jackson
(74) *Attorney, Agent, or Firm* — Rankin, Hill & Clark LLP

(57) ABSTRACT

In the assist device, the output of an actuator is adjusted so that it becomes lower as a state of charge of a battery exceeds a first threshold value, and also so that it becomes lower as the state of charge of the battery becomes lower. The output of the actuator is controlled on the basis of the state of charge of the battery, so that it is possible to make the agent recognize the change in the state of charge of the battery by changing the output of the actuator, and as a result, to avoid the situation where the agent feels strange with respect to stopping the operation of the assist device following thereto.

14 Claims, 4 Drawing Sheets

ASSIST DEVICE

BACKGROUND OF THE INVENTION

1. Field of the Invention

The present invention relates to a device for assisting a motion of an agent, by acting a force generated by an operation of an actuator to a body of the agent.

2. Related Background Art

Conventionally, in devices using a battery, various measures in response to the situation where a state of charge of the battery has decreased are being adopted. For example, in a power assist bicycle, there is proposed a technique of informing an assist travel available distance calculated on the basis of the state of charge of the battery (refer to Japanese Patent Laid-Open Publication No. H10-304502). Further, in an electric vehicle, there is proposed a technique of limiting an allowable discharge amount of the battery on the basis of the state of charge of the battery, in order to avoid the battery from running out during a journey (refer to Japanese Patent Laid-Open Publication No. 2005-271613).

However, in an assist device operating so as to assist a motion of or to relieve a body burden of an agent such as a human being, there is an especially high necessity for adjusting the operation state so as not to make the agent feel strange when the state of charge of the battery becomes insufficient.

SUMMARY OF THE INVENTION

The object of the present invention to provide an assist device capable of assisting a motion of an agent without making the agent feel strange.

To achieve the above object, the present invention provides an assist device including a power source, an actuator, and a control device for controlling an operation of the actuator by adjusting a supplied electricity from the power source to the actuator, for assisting a motion of or relieving a body burden of an agent by acting an output generated by the operation of the actuator to a body of the agent via a contact element; wherein the control device comprises: a state monitoring means which measures a state of charge of the power source or an available electricity thereof; a first control means which adjusts the output of the actuator, on condition that the state of charge of the power source or the available electricity thereof is equal to or less than a first threshold value, so that a motion assist rate of the assist device becomes lower than in the case where the state of charge of the power source or the available electricity thereof exceeds the first threshold value and also decrease by a greater degree as the state of charge of the power source or the available electricity thereof becomes lower; and a second control means which stops the operation of the actuator, on condition that the state of charge of the power source or the available electricity thereof is equal to or less than a second threshold value which is smaller than the first threshold value.

According to the assist device of the present invention, the output of the actuator is adjusted, on condition that the state of charge of the power source or the available electricity thereof is equal to or less than the first threshold value, so that the motion assist rate of the assist device becomes lower than in the case where the state of charge of the power source or the available electricity thereof exceeds the first threshold value, and also becomes lower as the state of charge of the power source or the available electricity thereof becomes lower. By adjusting either one of or both of an output oscillation and an output period of the actuator, it is possible to adjust the motion assist rate of the assist device. Thereafter, on condition that the state of charge of the power source or the available electricity thereof becomes equal to or less than the second threshold value which is smaller than the first threshold value, the operation of the actuator is stopped. The output of the actuator is controlled on the basis of the state of charge of the power source or the available electricity thereof, so that it is possible to make the agent recognize the change in the state of charge of the power source or the available electricity thereof by changing the output of the actuator, and as a result it is possible to avoid the situation where the agent feels strange with respect to the stopping of the operation of the assist device following thereto.

It is possible that the first control means sets the first threshold value to be higher as a power consumption of the actuator measured by the state monitoring means is higher, in the state where the state of charge of the power source or the available electricity thereof exceeds the first threshold value.

According to the assist device of such structure, when the motion of the agent is assisted in a manner in which the power consumption of the actuator is relatively high, the first threshold value is set to be relatively high. By doing so, in the situation where a relatively rapid decrease in the state of charge of the battery or the available electricity thereof is foreseen, the decrease of the motion assist rate of the assist device is commenced from a relatively early stage. Therefore, it is possible to avoid the situation where the state of charge of the battery or the available electricity thereof is excessively low immediately after the commencement of the decrease of the motion assist rate of the assist device, and as a result, it is possible to avoid the situation where the motion assist rate changes relatively greatly before and after the state of charge of the battery or the available electricity thereof becomes equal to or less than the first threshold value. Therefore, it is possible to avoid the situation where the agent feels strange with respect to the change of the operation mode of the assist device.

It is possible that the second control means sets the second threshold value to be higher as the power consumption of the actuator measured by the state monitoring means is higher, in the state where the state of charge of the power source or the available electricity thereof exceeds the second threshold value.

According to the assist device of such structure, when the motion of the agent is assisted in a manner in which the power consumption of the actuator is relatively high, the second threshold value is set to be relatively high. By doing so, in the situation where the state of charge of the power source or the available electricity thereof is decreasing relatively rapidly, the operation of the assist device is stopped relatively in an early stage. Therefore, it is possible to avoid the situation where the operation of the assist device is stopped at a timing different from the prediction of the agent realizing the relatively rapid decrease of the motion assist rate by the assist device, the prediction being the operation of the assist device be stopped relatively in an early stage. Therefore, it is possible to avoid the situation where the agent feels strange with respect to the change of the operation mode of the assist device.

It is possible that the first control means notifies to the agent the motion assist rate of the assist device, or an amount of change of the motion assist rate of the assist device compared to the state where the state of charge of the power source or the available electricity thereof exceeds the first threshold value, on condition that the state of charge of the power source or the available electricity thereof is equal to or less than the first threshold value.

According to the assist device of such structure, in the case where the state of charge of the power source or the available electricity thereof is equal to or less than the first threshold value, the motion assist rate of the assist device, or the amount of change of the motion assist rate of the assist device compared to the case where the state of charge of the power source or the available electricity thereof exceeds the first threshold value, is notified to the agent. By doing so, it is possible to avoid the situation where the agent feels strange with respect to the change in the output of the actuator set according to the change in the motion assist rate of the assist device.

It is possible that the second control means notifies to the agent the deficiency of the state of charge of the power source or the available electricity thereof, on condition that the state of charge of the power source or the available electricity thereof is equal to or less than the second threshold value.

According to the assist device of such structure, at a timing when the operation of the actuator is stopped, the fact that the state of charge of the power source or the available electricity thereof is insufficient is notified to the agent. By doing so, it is possible to avoid the situation where the agent feels strange with respect to the operation of the actuator being stopped.

It is possible that the state monitoring means measures the state of charge of the power source or the available electricity thereof, on the basis of an average value of the power consumption of the actuator for a predetermined time taking a motion period of the agent as a reference.

According to the assist device of such structure, in the situation where the periodical motion of the agent is being assisted, the state of charge of the power source or the available electricity thereof may be measured in an appropriate manner, in view of the fact that the power consumption of the actuator change in accordance with the repeating of the periodical motion. And by controlling the operation of the actuator on the basis of the state of charge of the power source or the available electricity thereof as mentioned above, it is possible to avoid the situation where the agent feels strange.

It is possible that the state monitoring means measures a physiological state variable representing a physiological state of the agent, and the second control means stops the operation of the actuator, on condition that the measured value of the physiological state variable deviates from a first range, the first range representing that the physiological state of the agent is normal.

According to the assist device of such structure, it is possible to prevent the agent from feeling strange, by continuing the operation of the assist device even though the physiological state of the agent is inappropriate for continuing the motion.

It is possible that the state monitoring means measure as the physiological state variable the pressure acting on the contact element.

According to the assist device of such structure, it is possible to prevent the agent from feeling strange, by continuing the operation of the assist device even though pressure applied from the contact element to the body of the agent is too tight or too strong.

It is possible that the state monitoring means measures an operation state variable representing an operation state of the power source or the actuator, and the second monitoring means stops the operation of the actuator, on condition that the measured value of the operation state variable deviates from a second range, the second range representing that the operation state of the power source or the actuator is normal.

According to the assist device of such structure, it is possible to avoid the situation where the agent feels strange by continuing the operation of the assist device, even though the battery or the actuator is in an abnormal condition, and as such the motion is not assisted properly.

It is possible that the state monitoring means measures as the available electricity of the power source a maximum current, a maximum voltage or a maximum electricity of the power source.

It is possible that, in the situation where the state of charge of the power source or the available electricity thereof is equal to or less than the first threshold value, the first control means decreases the motion assist rate of the assist device by decreasing the output of the actuator during a second period other than a first period among a motion period of the agent than in the situation where the state of charge of the power source or the available electricity thereof exceeds the first threshold value.

It is possible that the first control means decreases the motion assist rate of the assist device by shortening the first period in which the output of the actuator is relatively high among the motion period of the agent, and on the other hand extending the second period in which the output of the actuator is lower than in the first period.

It is possible that the assist device comprises a motor as the actuator, wherein the first control means breaks the movement of the agent by controlling the output of the motor during the second period to be in reverse polarity to the output of the motor during the first period, so as to generate a regenerative electric power by the motor.

It is possible that the first control means adjusts a motion state variable based on either one of or both of an oscillation and an angular velocity of a periodical motion of the agent, by adjusting a distribution of the first period and the second period in the motion period of the agent.

It is possible that the assist device is configured to assist a walking motion of the agent by assisting a cyclic movement of thighs of a human being as the agent, and wherein the first control means maintains a stride, a cadence, or a walking ratio of the agent as the motion state variable to a desired value, by adjusting the distribution of the first period and the second period in the motion period of the agent.

DETAILED DESCRIPTION OF THE PREFERRED EMBODIMENTS

Figure 1:
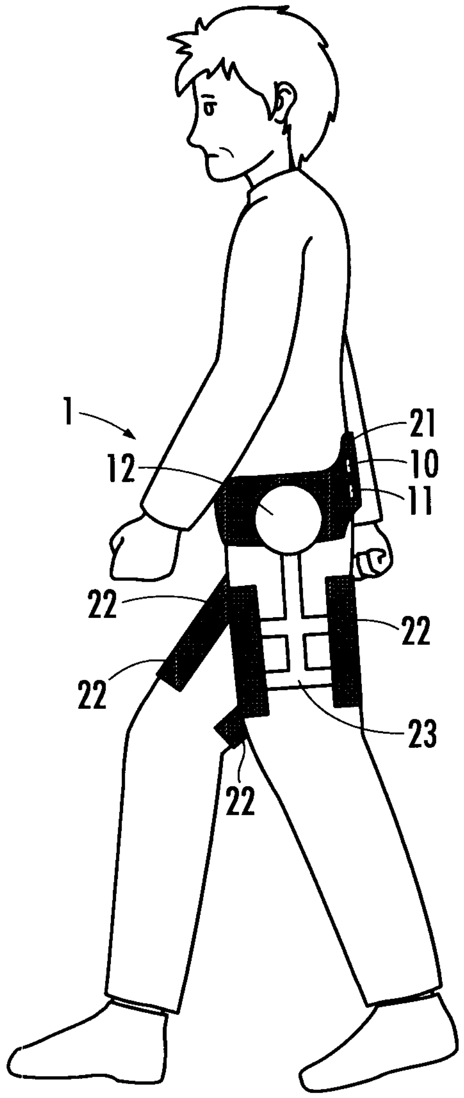
FIG. 1 is an explanational view showing the configuration of an assist device according to the present invention.
Figure 2:
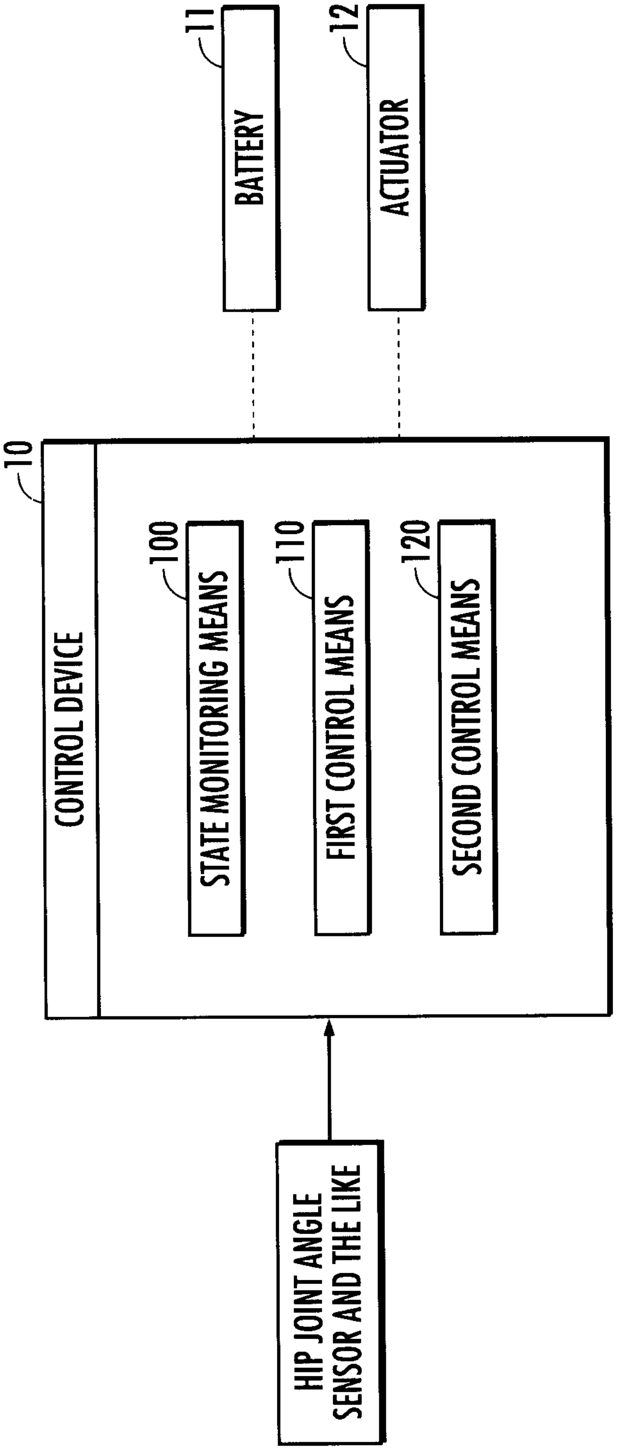
FIG. 2 is an explanational view showing the configuration of the assist device according to the present invention.

An embodiment of an assist device of the present invention will be described in detail hereinafter with reference to the accompanied drawings. First, explanation will be given on the configuration of the assist device. The assist device 1 shown in FIG. 1 is equipped with a control device 10, a battery (power source) 11, an actuator 12, a waist attachment (a first contact element) 21, and a thigh attachment (a second contact element) 22.

The waist attachment 21 is prepared by combining materials having rigidity and materials having flexibility, and is attached to the waist of an agent. The thigh attachment 22 is also prepared by combining materials having rigidity and materials having flexibility, and is attached to the front and rear of the thigh of the agent.

A link member 23 is prepared from materials having finite form such as a light-weight rigid plastic, take a bifurcated shapes toward the front and rear of the thigh after extending downward from the side of the waist of the agent along the thigh of the agent, and is connected to the actuator 12 and the front and rear thigh attachments 22, respectively.

The battery 11 is stored in the waist attachment 21 (for example, fixed between a plurality of sheets of the materials constituting the waist attachment 21), and supplies electricity to the actuator 12 and the like. The actuator 12 is installed to the waist attachment 21, and actuates force to the thigh of the agent via the link member 23 and the thigh attachment 22.

The control device 10 is configured from a computer (configured from a CPU, a ROM, a RAM, an I/O circuit, and an A/D conversion circuit and the like) stored in the waist attachment 21. The control device 10 controls the operation of the actuator 12, by reading out a program stored in a memory, and executing an arithmetic processing according to the program. For example, the control device 10 controls the operation of the actuator 12, so as to harmonize a motion rhythm of the agent and the operation rhythm of the assist device 1, on the basis of periodic signals output from a hip joint angle sensor (not shown) accompanied by the walking motion of the agent.

The control device 10 is equipped with a state monitoring means 100, a first control means 110, and a second control means 120.

The state monitoring means 100 measures the operation state and the like of the assist device 1. For example, the state monitoring means 100 measures the state of charge (available electricity) SOC of the battery 11. The first control means 110 adjusts the output of the actuator 12 on the basis of the state of charge SOC of the battery, on condition that the state of charge SOC of the battery 11 is equal to or less than a first threshold value SOC1. The second control means 120 stops the operation of the actuator 12, on condition that the state of charge SOC of the battery 11 is equal to or less than a second threshold value SOC2, which is smaller than the first threshold value SOC1.

Next, explanation will be given on the function of the assist device 1 of the above-mentioned structure.

Figure 3:
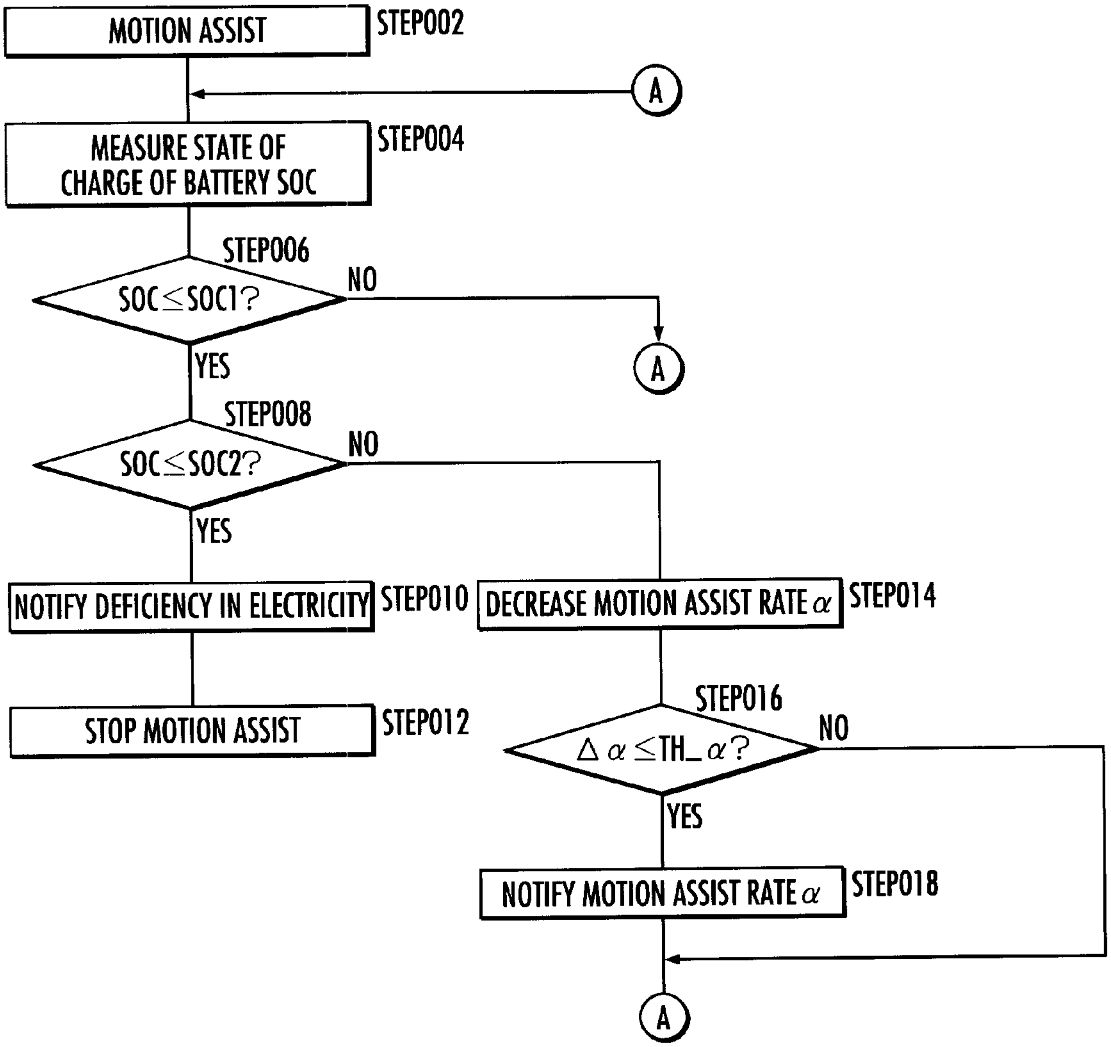
FIG. 3 is a flowchart indicating the function of the assist device according to the present invention.

First, with the operation of the actuator 12, the walking motion of the agent, more particularly a motion for moving the left and right thighs in the anteroposterior direction with respect to the waist, is being assisted (FIG. 3, STEP002). More specifically, the operation of the actuator 12 is controlled by the control device 10 by adjusting the supplied electricity from the battery 11 to the actuator 12 according to techniques disclosed in Japanese Patent No. 3950149, Japanese Patent No. 4008464, or Japanese Patent No. 4008465, and the like.

Here, it may be configured so that the value of motion state variable (stride, cadence, or walking ratio and the like) representing the motion state of the agent is measured by the state monitoring means 100, and the output of the actuator 12 is adjusted by the first control means 110 so that the measured value of the motion state variable of the agent coincides with the desired value. The stride is a motion variable representing the oscillation of a periodical motion or the walking motion of the agent. The stride may be calculated on the basis of a length of a leg of the agent (stored in the memory), and the maximum value of the hip joint angle (measured on the basis of the output signal of the hip joint angle sensor configured from a rotary encoder) in a bending direction (forward) and an stretching direction (rearward), respectively. The cadence (number of steps per unit time) is a motion state variable representing an angular velocity of the periodical motion of the agent. The cadence may be calculated on the basis of a landing timing of the left and right leg grasped by a temporal change pattern of the output signals of an acceleration sensor measuring an acceleration of the user in the vertical direction. The walking ratio is a motion state variable set on the basis of the oscillation and the angular velocity of the periodical motion of the agent. The walking ratio is calculated as a proportion of the cadence to the stride.

Further, the state of charge (available electricity) SOC of the battery 11 is measured by the state monitoring means 100 (FIG. 3, STEP004). For example, a voltage or an electric current of the battery 11 is measured, and the state of charge SOC of the battery is measured on the basis of this measurement result and a table or a calculated relational expression stored in a storage device or the memory.

Next, the state monitoring means 100 determines whether or not the state of charge SOC of the battery is equal to or less than the first threshold value SOC1 (FIG. 3, STEP006). Then, when it is determined that the state of charge SOC of the battery is equal to or less than the first threshold value SOC1 (FIG. 3, STEP 006: YES), then the state monitoring means 100 further determines whether or not the state of charge SOC of the battery is equal to or less than the second threshold value SOC2 (FIG. 3, STEP008). The second threshold value SOC2 is set from the viewpoint of making the temporal change pattern of the output of the actuator 12 coincide with the desired pattern to be explained later.

Here, when the state of charge SOC of the battery is determined to be higher than the first threshold value SOC1 (FIG. 3, STEP006: NO), the state monitoring means 100 continues to measure the state of charge SOC of the battery (FIG. 3, STEP004). As an alternate to the state of charge SOC of the battery 11, the maximum current, the maximum voltage, or the maximum electricity of the battery 11 may be measured as the available electricity of the battery 11 or an index value representing the available electricity. Further, an index value set on the basis of a part of or all of the maximum current, the maximum voltage, and the maximum electricity may be measured as the available electricity of the battery 11 or the index value representing the available electricity.

When it is determined that the state of charge SOC of the battery is equal to or less than the second threshold value SOC2 (FIG. 3, STEP008: YES), the second control means 120 output voice to the effect that the state of charge SOC of the battery is insufficient via an audio output device (not shown), so as to notify the agent (FIG. 3, STEP010). Thereafter, the second control means 120 stops the supplied electricity to the actuator 12, so that the operation of the actuator is stopped (FIG. 3, STEP012).

On the other hand, when it is determined that the state of charge SOC of the battery is higher than the second threshold value SOC2 (FIG. 3, STEP008: NO), the first control means 110 controls the operation of the actuator 12, so that a motion assist rate $\alpha$ by the assist device 1 becomes lower than in the case where the state of charge SOC of the battery is higher than the first threshold value SOC1 (FIG. 3, STEP014).

Figure 4:
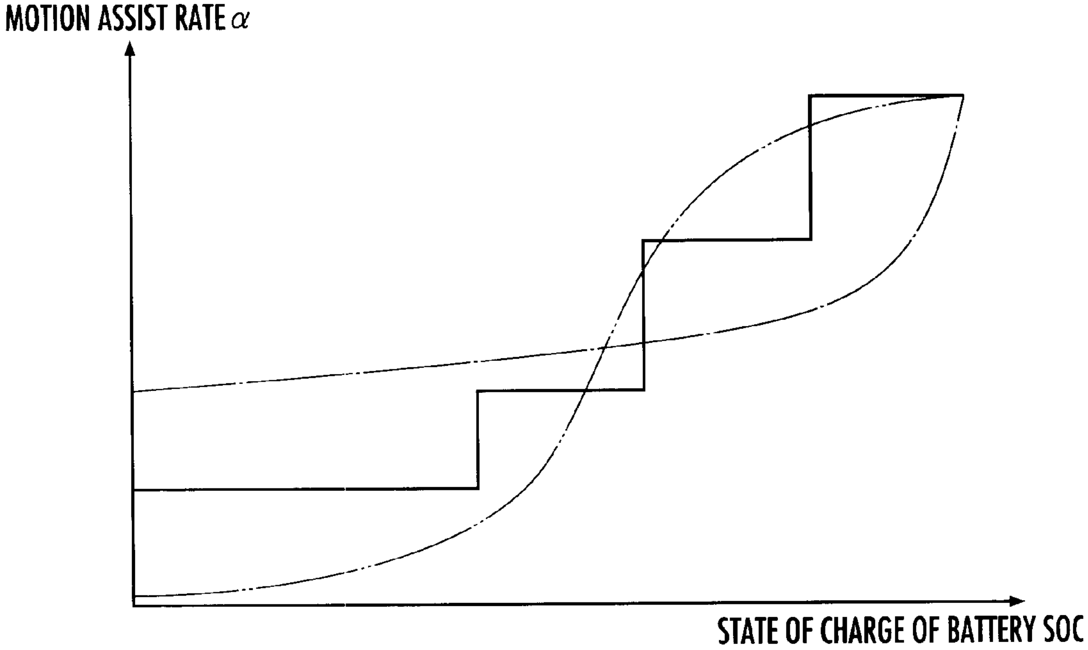
FIG. 4 is an explanational view in relation to an output control of an actuator.

More specifically, as shown in FIG. 4, the motion assist rate $\alpha$ is decided according to a function defined so that the motion assist rate $\alpha$ is lowered in a stepwise manner or continuously, as the state of charge SOC of the battery becomes lower. Thereafter, the supplied electricity to the actuator 12 is adjusted according to the motion assist rate $\alpha$ of the assist device 1. For example, a supplied current I or the temporal mean value thereof is adjusted to $\alpha^{1/2}$ so that a supplied electricity P to the actuator 12 (an average supplied electricity during a plurality of motion periods) in the case where the state of charge SOC of the battery is higher than the first threshold value SOC1 becomes αP. Here, during this process, it may be configured as mentioned above that the output of the actuator 12 is adjusted by the first control means 110 so that the measured value of the motion state variable of the agent coincides with the desired value.

For example, in the situation where the state of charge SOC of the battery became equal to or less than the first threshold value SOC1, by saving or reducing the output or a power consumption of the actuator 12 during a second period other than a first period of the motion period of the agent than in the situation where the state of charge SOC of the battery exceeds the first threshold value SOC1, the overall power consumption of the actuator 12 and the motion assist rate α of the assist device 1 may be decreased. Further, the motion assist rate α may be decreased by shortening the first period during which the output of the actuator 12 is relatively high in the motion period of the agent, and extending the second period during which the output of the actuator 12 is relatively low. That is, the motion assist rate α may be adjusted by adjusting a distribution of the first period and the second period in the walking cycle of the agent (set by a switching point in time from the first period to the second period, and a switching point in time from the second period to the first period).

Further, the first control means 110 may control the output of the actuator (motor) 12 during the second period to be in reverse polarity to the output of the actuator 12 during the first period, so as to brake the movement of the agent, generate regenerative electric power by the actuator 12, and use the regenerative electric power for the purpose of making the control device 10 function and the like. As a result of the decrease in the output of the actuator 12 during the second period as mentioned above, the output of the actuator 12 during the first period may be adjusted to be higher than the output of the actuator 12 during the second period. Alternatively, regardless of whether or not the state of charge SOC of the battery is equal to or less than the first threshold value SOC1, the output of the actuator 12 during the first period may be adjusted to be higher than the output of the actuator 12 during the second period. In this case, by setting a period in which the assist for moving the thigh is especially necessary as the first period, the stride and the like as the motion state variable may be maintained to the desired stride and the like even in the case where the motion assist rate α is decreased.

Further, the state monitoring means 100 determines whether or not an amount of change Δα of a current time motion assist rate with respect to a last time motion assist rate α of the actuator 12 (or the motion assist rate α in the case where the state of charge SOC of the battery is more than the first threshold value SOC1) is equal to or more than a set value TH_α (FIG. 3, STEP016). When it is determined that the amount of change Δα of the motion assist rate is equal to or more than the set value TH_α (FIG. 3, STEP016: YES), then the first control means 110 notifies to the agent the motion assist rate α or the amount of change Δα thereof (FIG. 3, STEP018). On the other hand, when it is determined that the amount of change Δα of the motion assist rate is less than the set value TH_α (FIG. 3, STEP016: NO), then the processing subsequent to the measurement of the state of charge SOC of the battery are repeated (FIG. 3, STEP002 and the like).

According to the assist device 1 exerting the above-mentioned function, on condition that the state of charge of the battery (or the available electricity from the power source to the actuator 12) SOC is equal to or less than the first threshold value SOC1, the output of the actuator 12 is adjusted so that it is lower than in the case where the state of charge SOC of the battery exceeds the first threshold value SOC1, and also it becomes lower as the state of charge SOC of the battery becomes lower (refer to FIG. 3, STEP006, STEP018, FIG. 4). Because the output of the actuator 12 is controlled on the basis of the state of charge SOC of the battery, it is possible to make the agent recognize the change in the state of charge SOC of the battery by changing the output of the actuator 12, and as a result it is possible to avoid the situation where the agent feels strange with respect to the stop in operation of the assist device 1 followed thereto. Further, on condition that the state of charge SOC of the battery is equal to or less than the first threshold value SOC1, the motion assist rate α or the amount of change Δα thereof is notified to the agent (refer to FIG. 3, STEP006, STEP018). By doing so, it is possible to avoid the situation where the agent feels strange with respect to the change in the output of the actuator 12 set according to the amount of the state of charge SOC of the battery.

Then, on condition that the state of charge SOC of the battery is equal to or less than the second threshold value SOC2, which is smaller than the first threshold value SOC1, the fact that the state of charge SOC of the battery is insufficient is notified to the agent, and the operation of the actuator 12 is stopped (refer to FIG. 3, STEP008 through STEP012). By doing so, it is possible to avoid the situation where the agent feels strange with respect to the stopping of the operation of the actuator 12.

Further, the output of the actuator 12 is adjusted so that the measured value of the motion state variable representing the motion state of the agent coincides with the desired value. Therefore, even when the motion assist rate α of the assist device 1 decreases according to the decrease in the power supplying ability of the battery 11, the agent is capable of carrying out the motion in a manner in which the value of the motion state variable coincides with the desired value, similarly to the situation before decrease in the motion assist rate α. Therefore, it is possible to dissolve or relieve the strangeness felt by the agent with respect to the change in the output of the actuator 12.

Further, the second threshold value SOC2 is set according to the capability of making the value of the motion state variable coincide with the desired value. Therefore, by stopping the operation of the actuator 12 on condition that the available electricity of the battery 11 is equal to or less than the second threshold value SOC2 as explained above, it is possible to stop the operation of the actuator 12 before reaching the condition that it is difficult for the assist device 1 to assist the motion of the agent in a manner in which the value of the motion state variable coincides with the desired value. Therefore, it is possible to dissolve or relieve the strangeness felt by the agent with respect to the change in the output of the actuator 12.

Here, various devices may be adopted as the assist device other than the assist device 1 shown in FIG. 1, such as a walking assist device disclosed in Japanese Patent Laid-Open No. 2007-020909, and various devices which assists the motion of the agent or which operates to relieve the body burden of the agent, for example, an electric bicycle.

Further, in the case where a capacitor or a fuel cell is adopted as the power source instead of or in addition to the battery 11, the available electricity of the power source may be measured according to the amount of the capacity of the capacitor or a remaining fuel of a hydrogen gas or the like of the fuel cell, instead of or in addition to the state of charge of the battery 11.

Still further, instead of or in addition to auditory perception, the decrease in the state of charge SOC of the battery or the motion assist rate α may be notified to the agent through a visual perception, a tactile perception, a taste sensation (preparation of chemical substances arranged so as to reach the tongue of the agent), or an olfactory perception (exposure of aromatic substances).

It is possible to make the agent recognize the motion assist rate α or the like of the assist device 1 through the visual perception by a flashing pattern of an LED, a color of a flashing light, a display of symbols or characters on a display panel, and the like. Further, it is possible to make the agent recognize the motion assist rate α or the like of the assist device 1 through the tactile perception by an existence or nonexistence of a vibration or a vibration pattern by a vibrating element, adjustment of the constriction of the thigh attachment 22 by an actuator (not shown), and the like. Still further, it is possible to make the agent recognize a motion assist available time Tass or the like of the assist device 1 through the taste sensation by introducing sugar or acid and the like to the mouth orifice of the agent. Still further, it is possible to make the agent recognize the motion assist rate α or the like of the assist device 1 through the olfactory perception by dispersing or exposing the aromatic substances and the like.

It may be configured so that the first control means 110 sets the first threshold value SOC1 to be higher as a power consumption Pcon of the actuator 12 measured by the state monitoring means 100 is higher, in the condition where the state of charge SOC of the battery (available electricity of the power source) exceeds the first threshold value SOC1.

According to the assist device 1 of such structure, when the motion of the agent is assisted in a manner in which the power consumption Pcon of the actuator 12 is relatively high, the first threshold value SOC1 is set to be relatively high. By doing so, in the situation where a relatively rapid decrease in the state of charge SOC of the battery is foreseen, the decrease of the motion assist rate α of the assist device 1 is commenced from a relatively early stage. Therefore, it is possible to avoid the situation where the state of charge SOC of the battery is excessively low immediately after the commencement of the decrease of the motion assist rate α of the assist device 1, and as a result, it is possible to avoid the situation where the motion assist rate α changes relatively greatly before and after the state of charge SOC of the battery becomes equal to or less than the first threshold value SOC1. Therefore, it is possible to avoid the situation where the agent feels strange with respect to the change of the operation mode of the assist device 1.

It may be configured so that the second control means 120 sets the second threshold value SOC2 to be higher as the power consumption Pcon of the actuator 12 measured by the state monitoring means 100 is higher, in the condition where the state of charge SOC of the battery (available electricity of the power source) exceeds the second threshold value SOC2. In the assist device 1 of such structure, when the motion of the agent is assisted in a manner in which the power consumption Pcon of the actuator 12 is relatively high, the second threshold value SOC2 is set to be relatively high.

By doing so, in the situation where the state of charge SOC of the battery is decreasing relatively rapidly, the operation of the assist device 1 is stopped at a relatively early stage. Therefore, it is possible to avoid the situation where the operation of the assist device 1 is stopped at a timing different from the prediction of the agent realizing the relatively rapid decrease of the motion assist rate α by the assist device 1, the prediction being the operation of the assist device be stopped at a relatively early stage. Therefore, it is possible to avoid the situation where the agent feels strange with respect to the change of the operation mode of the assist device 1.

It may be configured so that the state monitoring means 100 measures a physiological state variable (heart rate, blood pressure, electrodermal activity, myoelectric potential, brain wave, hemoglobin concentration of blood, exhaled breath oxygen concentration, and the like) representing a physiological state of the agent, and the second control means 120 stops the operation of the actuator 12, on condition that the measured value of the physiological state variable deviates from "a first range" which represents that the physiological state of the agent is normal.

By doing so, it is possible to avoid the situation where the agent feels strange by continuing the operation of the assist device 1, even though the physiological state of the agent is inappropriate for continuing the motion. Further, the state monitoring means 100 may measure the pressure applied to the waist attachment 21 or the thigh attachment 22 as the physiological state variable on the basis of the output signal of the pressure sensor. As a result, it is possible to avoid the situation where the agent feels strange by continuing the operation of the assist device 1 even though pressure applied from the waist attachment 21 or the thigh attachment 22 to the body of the agent is too tight or too strong.

It may be configured so that the state monitoring means 100 measures an operation state variable (a temperature of the battery 11 or a vibrational frequency of the actuator 12) representing the operation state of the battery 11 or the actuator 12, and the second control means 120 stops the operation of the actuator 12, on condition that the measured value of the operation state variable deviates from "a second range" which represents that the operation state of the battery 11 or the actuator 12 is normal.

By doing so, it is possible to avoid the situation where the agent feels strange by continuing the operation of the assist device 1, even though the battery 11 or the actuator 12 is in an abnormal condition, and as such the motion is not being assisted properly.

It may be configured that the motion assist available time Tass is notified to the agent, in addition to the motion assist rate α of the assist device 1 (refer to FIG. 3, S108). In this case, the state monitoring means 100 measures the power consumption Pcon of the actuator 12. For example, a time average value of the power consumption of the actuator 12 over one walking motion period or a plurality of walking motion periods of the agent (proportional to a square of the supply current to the actuator 12) may be measured as the power consumption Pcon of the actuator 12. The walking motion period of the agent may be measured by sensing a change cycle of the hip joint angle or the hip joint angular velocity of the agent, or a change cycle of a floor reaction force acted on the foot of the agent. Here, an accumulated power consumption during a predetermined period of the actuator 12 may be measured as the power consumption Pcon of the actuator 12.

Further, the state monitoring means 100 calculates the motion assist available time Tass of the assist device 1 on the basis of the state of charge SOC of the battery and the power consumption Pcon. More specifically, the motion assist available time Tass=f (SOC) is calculated according to a relational expression or a table defined so that the motion assist available time Tass continuously or intermittently becomes shorter as the state of charge SOC of the battery becomes lower and also the power consumption Pcon becomes higher. It is further determined whether or not a measurement time t being reset periodically reached a preset time Tset.

When it is determined that the measured time t reached the preset time Tset, the measured time t is reset to zero, and the motion assist available time Tass is notified to the agent by the first control means 110.

What is claimed is:

1. An assist device including a power source, an actuator, and a control device for controlling an operation of the actuator by adjusting a supplied electricity from the power source to the actuator, for assisting a motion of or relieving a body burden of an agent by acting an output generated by the operation of the actuator to a body of the agent via a contact element;

wherein the control device comprises:

a state monitoring means which measures a state of charge of the power source or an available electricity thereof;

a first control means which adjusts the output of the actuator, on condition that the state of charge of the power source or the available electricity thereof is equal to or less than a first threshold value, so that a motion assist rate of the assist device becomes lower than in a case where the state of charge of the power source or the available electricity thereof exceeds the first threshold value and also decreases by a greater degree as the state of charge of the power source or the available electricity thereof becomes lower; and a second control means which stops the operation of the actuator, on condition that the state of charge of the power source or the available electricity thereof is equal to or less than a second threshold value which is smaller than the first threshold value, wherein the first control means decreases the motion assist rate of the assist device by shortening a first period in which the output of the actuator is relatively high among a motion period of the agent, and on the other hand extending a second period in which the output of the actuator is lower than in the first period, wherein the assist device comprises a motor as the actuator, and wherein the first control means breaks the movement of the agent by controlling the output of the motor during the second period to be in reverse polarity to the output of the motor during the first period, so as to generate a regenerative electric power by the motor.

2. The assist device according to claim 1, wherein in the situation where the state of charge of the power source or the available electricity thereof is equal to or less than the first threshold value, the first control means decreases the motion assist rate of the assist device by decreasing the output of the actuator during a second period other than a first period among a motion period of the agent than in the situation where the state of charge of the power source or the available electricity thereof exceeds the first threshold value.

3. The assist device according to claim 2, wherein the first control means adjusts a motion state variable based on either one of or both of an oscillation and an angular velocity of a periodical motion of the agent, by adjusting a distribution of the first period and the second period in the motion period of the agent.

4. The assist device according to claim 3, wherein the assist device is configured to assist a walking motion of the agent by assisting a cyclic movement of thighs of a human being as the agent, and wherein the first control means maintains a stride, a cadence, or a walking ratio of the agent as the motion state variable to a desired value, by adjusting the distribution of the first period and the second period in the motion period of the agent.

5. The assist device according to claim 2, wherein in the situation where the state of charge of the power source or the available electricity thereof is equal to or less than the first threshold value, the first control means decreases the motion assist rate of the assist device by decreasing the output of the actuator during only the second period from among the first period and second period, as compared to the situation where the state of charge of the power source or the available electricity thereof exceeds the first threshold value.

6. The assist device according to claim 1, wherein the state monitoring means measures a physiological state variable representing a physiological state of the agent, and the second control means stops the operation of the actuator, on condition that the measured value of the physiological state variable deviates from a first range, the first range representing that the physiological state of the agent is normal.

7. The assist device according to claim 6, wherein the state monitoring means measure as the physiological state variable the pressure acting on the contact element.

8. The assist device according to claim 1, wherein the first control means sets the first threshold value to be higher as a power consumption of the actuator measured by the state monitoring means is higher, in the state where the state of charge of the power source or the available electricity thereof exceeds the first threshold value.

9. The assist device according to claim 1, the second control means sets the second threshold value to be higher as the power consumption of the actuator measured by the state monitoring means is higher, in the state where the state of charge of the power source or the available electricity thereof exceeds the second threshold value.

10. The assist device according to claim 1, wherein the first control means notifies to the agent the motion assist rate of the assist device, or an amount of change of the motion assist rate of the assist device compared to the state where the state of charge of the power source or the available electricity thereof exceeds the first threshold value, on condition that the state of charge of the power source or the available electricity thereof is equal to or less than the first threshold value.

11. The assist device according to claim 1, wherein the second control means notifies to the agent the deficiency of the state of charge of the power source or the available electricity thereof, on condition that the state of charge of the power source or the available electricity thereof is equal to or less than the second threshold value.

12. The assist device according to claim 1, wherein the state monitoring means measures the state of charge of the power source or the available electricity thereof, on the basis of an average value of the power consumption of the actuator for a predetermined time taking a motion period of the agent as a reference.

13. The assist device according to claim 1, wherein the state monitoring means measures an operation state variable representing an operation state of the power source or the actuator, and the second monitoring means stops the operation of the actuator, on condition that the measured value of the operation state variable deviates from a second range, the second range representing that the operation state of the power source or the actuator is normal.

14. The assist device according to claim 1, wherein the state monitoring means measures as the available electricity of the power source a maximum current, a maximum voltage or a maximum electricity of the power source.

* * * * *